United States Patent [19]
Blake, III

[11] Patent Number: 5,662,615
[45] Date of Patent: Sep. 2, 1997

[54] VALVE AND VALVE CARTRIDGE FOR TROCAR

[76] Inventor: Joseph W. Blake, III, 77 Locust Ave., New Canaan, Conn. 06840

[21] Appl. No.: 523,108

[22] Filed: Sep. 1, 1995

[51] Int. Cl.$^6$ .................................................. A61M 29/02
[52] U.S. Cl. .......................... 604/167; 604/164; 604/169
[58] Field of Search .................................. 604/161, 164, 604/167, 169; 251/149.1

[56] References Cited

U.S. PATENT DOCUMENTS

| | | | |
|---|---|---|---|
| 4,655,752 | 4/1987 | Honkanen | 604/167 |
| 4,960,412 | 10/1990 | Fink | 604/167 |
| 4,978,341 | 12/1990 | Niederhauser | 604/167 |
| 5,158,553 | 10/1992 | Berry | 604/169 |
| 5,350,364 | 9/1994 | Stephens | 604/167 |

*Primary Examiner*—Sam Rimell
*Assistant Examiner*—Luke J. Yeh
*Attorney, Agent, or Firm*—Patrick J. Walsh

[57] ABSTRACT

A sealing arrangement for trocar tubes including an upper ring seal forming the primary seal, and a lower seal valve forming the secondary seal. Both seals form part of a valve system which can be positioned within a removable cartridge. The valve cartridge comprises a tubular open-ended housing in which the seal ring is fitted to the top opening, and with the seal valve located within the housing. The seal valve is elastomeric in tubular form for passing instruments and is provided with upper and lower flanges for placement within the cartridge. The intermediate portion of the valve between the flanges is in the general form of converging and diverging frusto-conical sections which join along a sealing line. A seal is formed between the interior wall surfaces of the valve and the instrument present in the trocar tube. Peritoneal pressure is admitted to the trocar head or housing for pressing the valve in forming the desired seal. With the instrument removed, the valve walls engage each other along the seal line to form the desired seal. The valve walls are layered with hydrogel and a microencapsulated liquid coating substantially extending the shelf-life of the valve, providing lubricity for the valve surface, and improving the sealing characteristic of the base elastomer of the valve body.

15 Claims, 3 Drawing Sheets

VALVE AND VALVE CARTRIDGE FOR TROCAR

BACKGROUND OF THE INVENTION

The present invention relates to surgical instruments and particularly to an improved seal arrangement for a trocar tube.

A conventional trocar assembly comprises two basic interfitting, separable components: a trocar obturator subassembly and a trocar tube subassembly. The trocar obturator subassembly includes a supporting head with an elongate obturator having a tip. The tip can be a blunt or sharpened cutting tip and the tip is sometimes provided with a protective shield. The trocar tube includes a head and a depending tube together with a sealing arrangement within the head for closing and sealing the tube when it is in position during surgery. The assembly includes the trocar obturator interfitting the trocar tube with the tip projecting from the end of the tube and, if desired, being covered by the protective shield.

In ordinary use the trocar assembly penetrates a body cavity and the trocar obturator subassembly is withdrawn leaving the trocar tube in place for introducing other instruments into the body according to the requirements of a particular medical procedure. The trocar tube is provided with a sealing arrangement to close the tube in order to maintain the gas pressure within the body cavity as required for the medical procedure.

My U.S. Pat. No 5,242,412 discloses a seal for a trocar assembly, and in the Background of the Invention, the patent describes conventional sealing arrangements for trocar tubes.

The primary task of a trocar seal is to maintain pneumoperitoneal pressure while an operating instrument is present in the trocar tube, while the instrument is being inserted or removed, and after removal. In some cases the trocar double seal within the trocar tube includes an upper seal in the form of a sealing ring and a lower sealing valve.

Surgical instruments pass through the upper and lower seals giving rise to the hazard of the instrument injuring or disturbing the proper sealing position of one of the seals particularly the lower seal within the trocar tube housing. This hazard is present in the cases of disposable as well as non-disposable trocar tubes. Non-disposable trocar tubes are intended for reuse after sterilization and the opportunity arises for gradual weakening and ultimate failure of the lower seal by reason of exposure to repeated passing of surgical instruments.

The present invention provides an improved sealing arrangement for trocars in order to guard against seal failure due to instrument manipulation through the trocar, and to provide a seal cartridge that can be replaced periodically or after each use of the trocar for a single surgical procedure.

The present invention provides an inexpensive sealing arrangement for trocars with no moving parts in either of the upper and lower seals. This results in low manufacturing cost and feasibility of disposable trocar designs.

The invention also provides for improving the operating characteristics of the valve particularly its ready-to-use capability without the need to prehydrate before use, as well as valve surface lubricity and sealing characteristics.

SUMMARY OF THE INVENTION

The present invention comprises a sealing arrangement for trocar tubes including an upper ring seal forming the primary seal, and a lower seal valve forming the secondary seal.

In a preferred form of the invention, both seals form part of a valve cartridge. The valve cartridge is removable from the trocar tube and can be replaced as desired for reuse of the trocar tube. The valve cartridge comprises a tubular open-ended housing in which the seal ring is fitted to the top opening, and with the seal valve located within the housing. The seal valve is preferably elastomeric and tubular in form for passing instruments and is provided with upper and lower flanges for placement within the cartridge. The intermediate portion of the valve between the flanges is in the general form of converging and diverging frusto-conical sections or panels which come into contact with each other along a sealing line. A seal is formed by contacting interior wall surfaces of the valve before an instrument enters the trocar tube. Peritoneal pressure is admitted to the trocar head or housing for pressing the valve walls together in forming the desired seal.

When an instrument is introduced into the trocar tube, the upper ring seal engages the periphery of the instrument to maintain the desired peritoneal pressure within the trocar tube.

The valve cartridge is vented within the trocar housing to admit peritoneal pressure to the seal valve exterior.

The lower or diverging frusto-conical portion of the valve maintains the sealing integrity of the valve by preventing instrument snags that disturb the proper sealing position of the seal valve as instruments are removed from the trocar tube.

The sealing arrangement further includes an insert positioned within the seal valve in axial alignment with the valve passage to protect the valve wall interior surfaces from injury or puncture as an instrument passes in and out of the trocar tube. The insert protects the side walls without interfering with their normal sealing function.

In another preferred form of the invention, the sealing arrangement for trocar tubes including the upper ring seal forming the primary seal, and the lower seal valve forming the secondary seal are built into the trocar tube so that the entire trocar tube can be discarded after a single use.

In another aspect of the invention, the surfaces of the primary seal and the interior surface of the lower seal valve are coated with a hydrogel layer which, when hydrated as by absorbtion of water, fluffs up and becomes very slippery, i.e., provides a lubricious surface. The hydrating liquid absorbed by hydrogel gradually evaporates thereby depriving the hydrogel of its desired lubricious surface and severely limiting the shelf life of the product.

In accordance with the invention, the hydrogel layer is preferably applied to the elastomeric substrate in a dry or nonhydrated condition and the hydrogel layer is then covered with a microencapsulated liquid suitable for hydrating the hydrogel. The microencapsulated liquid remains dormant and the hydrogel in dry (i.e., non-hydrated) condition until the liquid is released from microencapsulation when the microcapsules are ruptured by an impinging object such as an instrument passing through the primary seal or lower seal valve interior. When the microencapsulated cells are ruptured, the contained liquid is released to activate the hydrogel coating thereby providing the desired slippery surface condition on the base material of the seal surfaces.

In this way, the microencapsulated liquid coating for the hydrogel layered valve substantially extends the shelf life of the trocar, provides lubricity for the seal surfaces precisely at the moment of need, and improves the sealing characteristic of the base elastomer of the valve body.

OBJECTS OF THE INVENTION

It is an object of the invention to provide a primary and secondary sealing arrangement for a trocar tube.

It is an object of the invention to provide a low cost primary and secondary sealing arrangement for a trocar tube.

It is an object of the invention to provide a seal cartridge for a trocar tube.

It is a further object of the invention to provide a seal valve for a trocar tube which resists deformation and loss of sealing integrity induced by instruments passing through the valve.

It is a further object of the invention to provide a protective insert for trocar seal valves.

It is a further object of the invention to provide a disposable trocar tube.

It is another object of the invention to provide hydrogel layered seals for trocar tubes wherein, by hydrating the hydrogel, the lubricity and sealing characteristics of the trocar are improved.

It is a further object of the invention to provide a microencapsulated liquid coating for a hydrogel layered valve to achieve a valve that is ready-to-use even after extended shelf life, to provide lubricity for the valve surface, and to improve the sealing characteristic of the base elastomer of the valve body.

Other and further objects of the invention will occur to one skilled in the art with an understanding of the following detailed description of the invention or upon employment of the invention in practice.

DESCRIPTION OF THE DRAWING

A preferred embodiment of the invention has been chosen for purposes of illustrating the construction and operation of the invention and is shown in the accompanying drawing in which.

DETAILED DESCRIPTION OF THE INVENTION

Figures 1, 2:
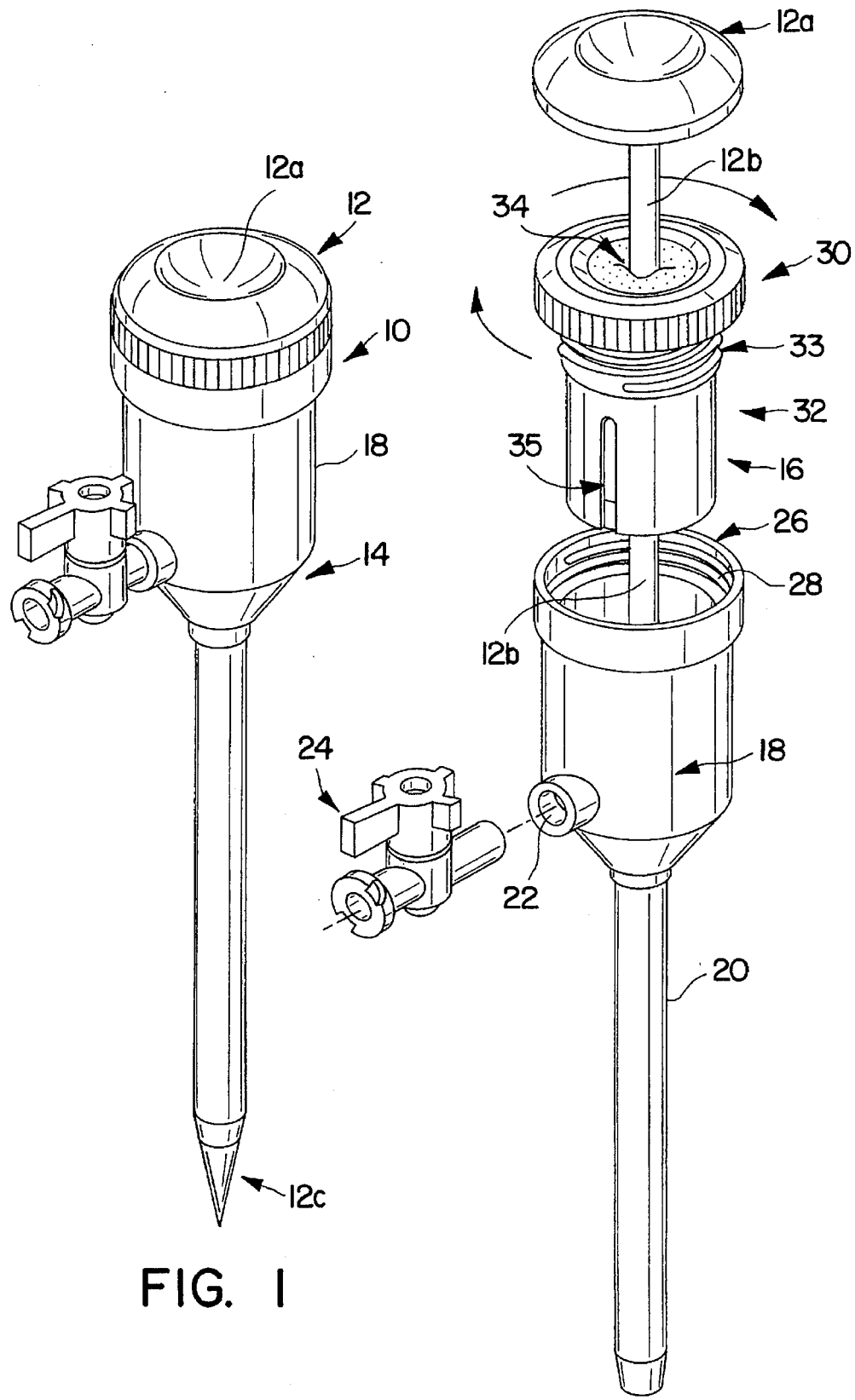
FIG. 1 is a perspective view of an assembled trocar.
FIG. 2 is an exploded perspective view of the components of the trocar of FIG. 1.

Referring now to FIGS. 1 and 2 of the drawing, an assembled trocar 10 according to the invention comprises a trocar obturator 12, a trocar tube 14, and a valve cartridge 16.

The trocar obturator comprises a head 12a, an elongate shaft 12b extending downwardly from the head and terminating in a trocar tip 12c.

The trocar tube includes an upper shell or housing 18 and a depending tube 20 through which pass the trocar obturator and surgical instruments (not shown) for endoscopic surgery. The housing has a port 22 (which may be fitted with a stop clock 24) used for insufflating and desufflating an abdominal cavity, for example, through the trocar tube. The upper shell is shown cylindrical in shape, however, it can be any suitable shape, box-like for example. The shell has an opening 26 at its upper end and has an internally threaded flange 28 or other suitable fastening means to receive and secure the valve cartridge 16 according to the invention.

Figure 7:
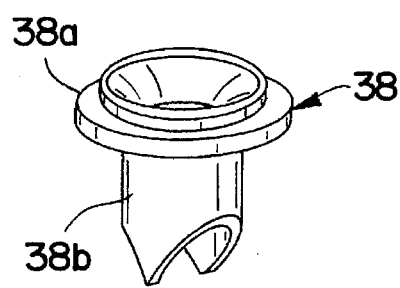
FIG. 7 is a perspective view of a cartridge insert.

The cartridge comprises an upper collar 30 and a depending cylindrical skirt 32 for receiving and positioning primary 34 and secondary seals 36 (FIG. 4) and the protective insert 38 (FIGS. 3 & 7) for the secondary seal, for attachment to the shell, for defining a sealed axial passage for the trocar as well as instruments passed through the trocar tube, and for admitting peritoneal pressure to the exterior surfaces of the secondary seal.

Figure 3:
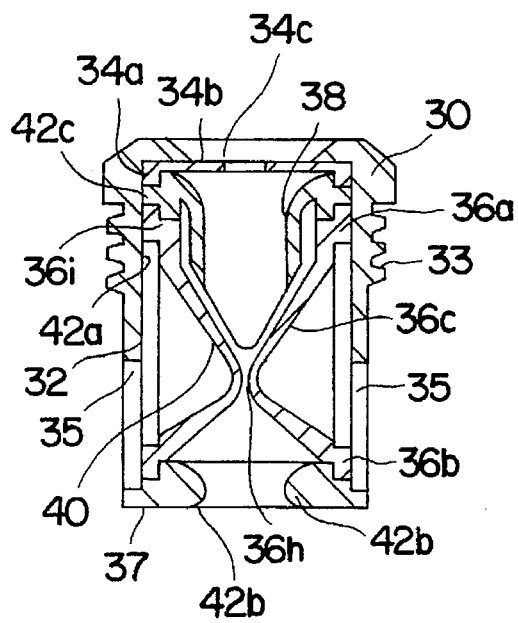
FIG. 3 is a vertical section view of the valve cartridge shown in FIG. 2.
Figure 4:
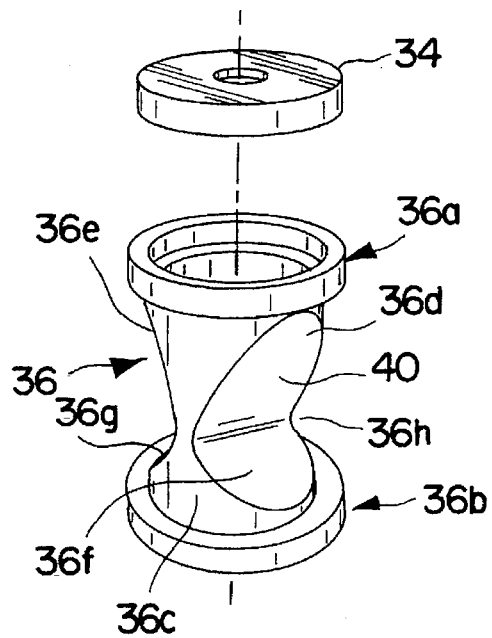
FIG. 4 is a perspective view of the primary and secondary seal members for use in a trocar tube.

The exterior and interior elements of the cartridge assembly are shown in FIGS. 2 and 3 and include cap or collar 30 and subjacent threaded section 33 for securing the cartridge to the trocar shell. The remaining skirt portion 32 of the cartridge is long enough to cover entirely the secondary seal valve while having vents 35 for the purpose of admitting peritoneal pressure to the exterior surface 40 of the secondary seal. The vents are preferably in the form of slits extending upward from the bottom edge 37 of the skirt best shown in FIG. 2, it being understood that other shaped openings in the skirt may be used for venting.

The interior surface of the cartridge has inwardly extending concentric ledges or rims 42a, 42b and 42c for supporting the primary and secondary seals.

Figure 8:
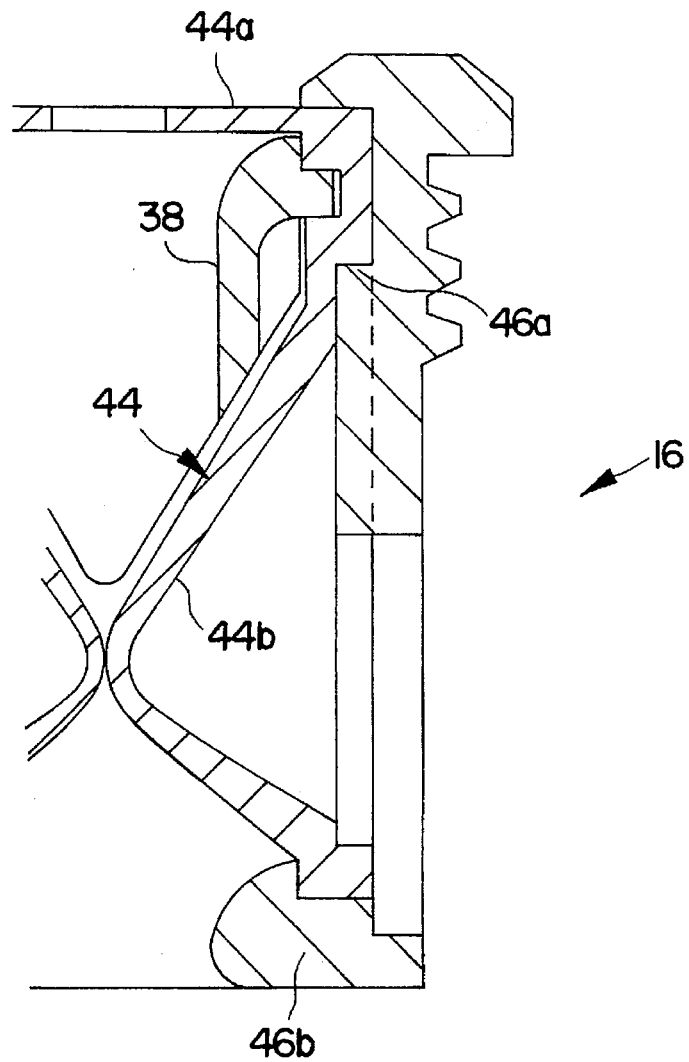
FIG. 8 is a modified form of the cartridge and primary and secondary seals.

A modified form of the cartridge and primary and secondary seals is shown in FIG. 8 in which the primary 44a and secondary 44b seals are a one piece molding 44 supported by inwardly extending rims 46a and 46b. A protective insert 38 shown also in FIG. 8 may be fitted inside the molding 44 for protecting the secondary seal 44b in a manner similar to protection of the embodiment of FIG. 3.

Figure 6:
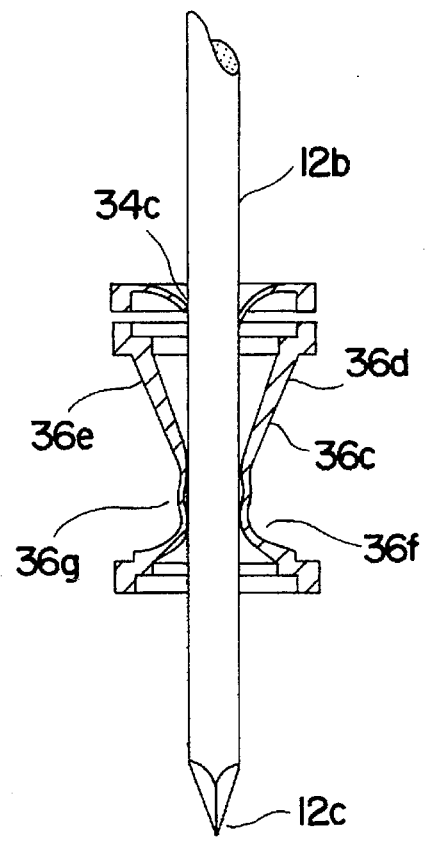
FIG. 6 is a vertical section view of the seal members of FIG. 5 with an instrument passing through the trocar tube.

The primary seal 34 is positioned on the upper ledge 42c of the cartridge. The primary seal includes a peripheral rim 34a which may be of square cross-section, and a radially extending annular sealing web 34b having a central aperture 34c of a diameter less than that of the trocar shaft and instruments passing through the trocar tube. As shown in FIG. 6, the elastic or elastomeric web 34c deflects and engages the trocar shaft 12b in a sealing relationship for maintaining peritoneal pressure within the trocar tube when the trocar shaft or an instrument is present.

Figure 5:
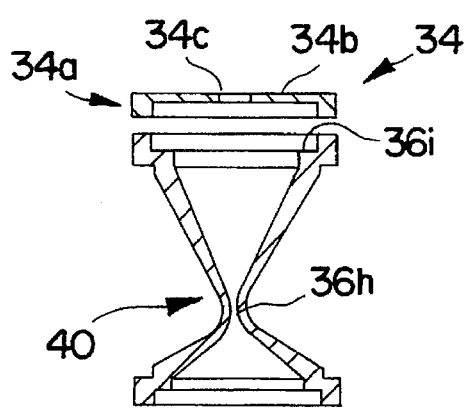
FIG. 5 is a vertical section view of the seal members of FIG. 3.

The secondary seal 36 is preferably elastomeric and is positioned on intermediate and lower interior ledges 42a and 42b of the cartridge skirt which respectively support upper and lower peripheral rims or flanges 36a and 36b of the secondary valve. The valve rims are joined by a generally cylindrical air tight tube 36c. The intermediate tube portion of the valve between the flanges is in the general form of converging 36d and 36e and diverging 36f and 36g planar wall sections which join along a sealing line 36h (FIG. 5). Beginning at opposite sides of the tube just below the upper flange, the tube walls 36d and 36e on each side are planar with opposite upper planar walls converging downwardly toward the seal line 36h defined by touching interior surfaces of the planar wall sections.

Beginning at the seal line, the lower opposite planar side walls 36f and 36g diverge outwardly and downwardly from the upper planar walls rejoining the tubular wall just above the lower flange. The lower planar walls comprise return panels which protect the integrity of the seal line by resisting the tendency of instruments to disturb the seal line by inverting the upper planar walls when passing through the seal valve. The secondary seal is a one-piece molded elastomeric valve which is air tight with a wall thickness sufficient to withstand and maintain peritoneal overpressure within the trocar shell.

The valve cartridge further includes a protective insert 38 of rigid lightweight plastic having a peripheral rim 38a and a depending truncated skirt 38b. The insert is placed within the seal valve on a ledge 36i formed therein with its protective skirt protecting the sidewalls of the valve against puncture, and acting as a guide for directing the trocar shaft and instruments with sharp tips to pass axially through the trocar tube and seal without puncturing the seal.

In another aspect of the invention, the valve and sealing ring are preferably elastomeric and provided with a hydrogel coating that absorbs water and makes the valve and ring very slippery in order to enhance their resistance to cutting or puncture by a passing trocar shaft or instrument.

Figure 9:
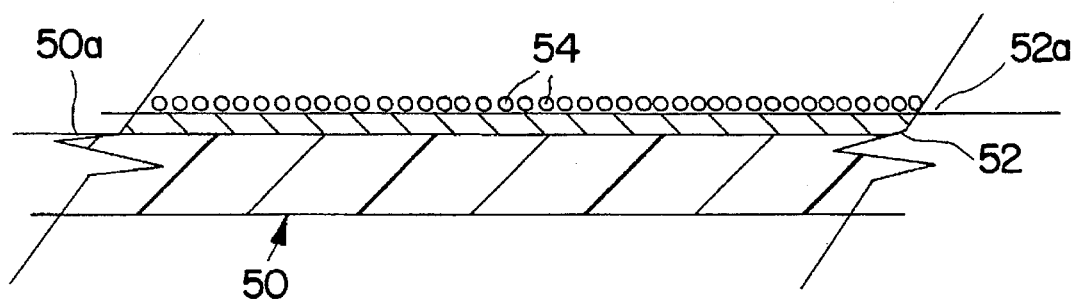
FIG. 9 is a schematic illustration of a sealing surface substrate coated with a hydrogel layer and with a microencapsulated liquid for hydrating the hydrogel.

Referring to FIG. 9, an elastomeric substance 50 such as polyurethane, silicone, latex, nitrile, thermoplastic elastomer or a host of other similar materials may be used for fabricating the valve and sealing ring. The interior surface 50a of the valve or ring is coated with a hydrogel layer 52 which, when hydrated as by absorbtion of water, fluffs up and becomes very slippery, i.e., provides a lubricious surface. In accordance with the invention, the hydrogel layer is preferably applied to the elastomeric substrate in a dry or non-hydrated condition. The outer surface 52a of the hydrogel layer is then covered with a microencapsulated liquid 54 suitable for hydrating the hydrogel. The microencapsulated liquid remains dormant and the hydrogel in dry (i.e., non-hydrated) condition until the liquid is released from microencapsulation. The microencapsulated liquid is any suitable liquid for hydration of the hydrogel such as water, saline solution, alcohol and so forth.

The period of dormancy extends from time of manufacture until the trocar employing the valve is placed in service. When a trocar shaft or instrument moving through the central passage of the trocar strikes the valve interior surface or sealing ring, the microcapsules are ruptured immediately releasing liquid in quantity sufficient to hydrate the hydrogel resulting in a lubricious valve surface for passing the instrument without puncturing or marring the sealing surface.

It is to be noted in particular that the instrument or trocar shaft strikes the valve walls in the vicinity of the sealing line 36h thereby releasing liquid for hydrating the hydrogel surface along the sealing line to improve the sealing characteristic of the base valve material.

In this way, the microencapsulated liquid coating for the hydrogel layered valve provides a ready-to-use trocar even after elapse of a long shelf life of the trocar. With the microencapsulated liquid coating, it is not necessary for the surgeon to independently hydrate the hydrogel immediately prior to use. The microencapsulated coating provides lubricity for the valve surface precisely at the moment of need, and improves the sealing characteristic of the base elastomer of the valve body.

I claim:

1. A trocar tube for receiving trocar obturators and surgical instruments, the trocar tube comprising a housing in the form of a hollow shell with aligned first and second openings in opposite sides of the housing defining a central passage therethrough, the first opening being in the top side of the shell, the second opening being in the bottom side, a tube depending from the second opening, the tube having an axis aligned with the central passage, a cartridge removably nested within the housing in alignment with the central passage, the cartridge having an upper collar and a depending cylindrical skirt, means for securing the cartridge to the first opening of the housing, a primary seal positioned in the cartridge around the first opening and encompassing the central passage, a secondary seal positioned in the cartridge within the skirt to encompass the central passage, the secondary seal having upper and lower peripheral rims joined by a generally cylindrical air tight tube, the tube portion of the valve between the rims being in the general form of upper converging and lower diverging planar wall sections which meet along a diametric sealing line defined by touching interior surfaces of the planar wall sections, the lower planar walls comprising return planar walls which protect the integrity of the seal line by resisting the tendency of instruments to disturb the seal line by inverting the upper planar walls when passing through the seal valve.

2. A trocar tube as defined in claim 1 in which the exterior of the cartridge is vented to the interior of the trocar tube shell.

3. A trocar tube as defined in claim 1 in which the shell and tube are integral.

4. A trocar tube for receiving a trocar obturator and instruments, the trocar tube comprising a housing in the form of a hollow shell with aligned first and second openings in opposite sides of the housing defining a central passage therethrough, the first opening being in the top side of the shell, the second opening being in the bottom side and having a tube affixed thereto, the tube having an axis aligned with the central passage, a cartridge removably nested within the housing in alignment with the central passage, the cartridge having an upper collar and a depending cylindrical skirt, means for securing the cartridge to the first opening of the housing, a primary seal positioned in the cartridge around the first opening and encompassing the central passage, a secondary seal positioned in the cartridge within the skirt to encompass the central passage, the secondary seal having upper and lower peripheral rims joined by a generally cylindrical air tight tube, the tube portion of the valve between the rims being in the general form of upper converging and lower diverging planar wall sections which meet along a diametric sealing line defined by touching interior surfaces of the planar wall sections the lower planar walls comprising return panels which protect the integrity of the seal line by resisting the tendency of instruments to disturb the seal line by inverting the upper planar walls when passing through the seal valve, and a protective insert having a peripheral rim and a depending truncated skirt placed within the secondary seal with its skirt protecting the sidewalls of the seal against puncture, and acting as a guide for directing instruments with tips to pass axially through the trocar tube and seal without puncturing the secondary seal.

5. A trocar tube as defined in claim 4 in which the exterior of the cartridge is vented to the interior of the trocar tube shell.

6. A trocar tube as defined in claim 1 in which the primary seal includes a peripheral rim, and a radially extending annular sealing web having a central aperture of a diameter less than that of instruments passing the trocar tube.

7. A trocar tube as defined in claim 1 in which the interior surface of the cartridge is provided with ledges for supporting the primary and secondary seals.

8. A trocar tube as defined in claim 4 in which the interior surface of the cartridge is provided with ledges for supporting the primary and secondary seals, and in which the insert is supported by the upper rim of the secondary seal.

9. A valve cartridge for a trocar tube of the type for receiving trocar obturators and instruments with the trocar tube having a housing in the form of a hollow shell with aligned first and second openings in opposite sides of the housing defining a central passage therethrough, the first opening being in the top side of the shell, the second opening being in the bottom side and having a tube affixed thereto, the tube having an axis aligned with the central passage, the cartridge comprising:
    i. an upper collar and a depending cylindrical skirt and being adapted for nesting within a trocar housing in alignment with the central passage, the upper collar and upper portion of the skirt having means for securing the cartridge to the first opening of a trocar housing,
    ii. a primary seal positioned in the cartridge around the first opening and encompassing the central passage,
    iii. a secondary seal positioned in the cartridge within the skirt to encompass the central passage, the secondary seal having upper and lower peripheral rims joined by a generally cylindrical air tight tube, the tube portion of the valve between the rims being in the general form of upper converging and lower diverging planar wall sections which meet along a diametric sealing line defined by touching interior surfaces of the planar wall sections the lower planar walls comprising return planar walls which protect the integrity of the seal line by resisting the tendency of instruments to disturb the seal line by inverting the upper planar walls when passing through the seal valve.

10. A valve cartridge as defined in claim 9 which further includes a protective insert having a peripheral rim and a depending truncated skirt placed within the secondary seal with its skirt protecting the sidewalls of the seal against puncture, and acting as a guide for directing instruments with tips to pass axially through the trocar tube and seal without puncturing the secondary seal.

11. A valve cartridge as defined in claim 9 in which the interior surface of the cartridge is provided with ledges for supporting the primary and secondary seals.

12. A valve cartridge as defined in claim 10 in which the interior surface of the cartridge is provided with ledges for supporting the primary and secondary seals, and in which the insert is supported by the upper rim of the secondary seal.

13. A valve cartridge as defined in claim 9 in which the exterior of the cartridge is open to the interior of a trocar tube shell.

14. A trocar tube for receiving trocar obturators and surgical instruments, the trocar tube comprising a housing in the form of a hollow shell with aligned first and second openings in opposite sides of the housing defining a central passage therethrough, the first opening being in the top side of the shell, the second opening being in the bottom side and having a tube affixed thereto, the tube having an axis aligned with the central passage, a primary seal positioned in the housing around the first opening and encompassing the central passage, a secondary seal positioned in the housing to encompass the central passage, the secondary seal having upper and lower peripheral rims joined by a generally cylindrical air tight tube, the tube portion of the valve between the rims being in the general form of upper converging and lower diverging planar wall sections which meet along a diametric sealing line defined by touching interior surfaces of the planar wall sections the lower planar walls comprising return planar walls which protect the integrity of the seal line by resisting the tendency of instruments to disturb the seal line by inverting the upper planar walls when passing through the seal valve.

15. A trocar tube for receiving trocar obturators and surgical instruments, the trocar tube comprising a housing in the form of a hollow shell with aligned first and second openings in opposite sides of the housing defining a central passage therethrough, the first opening being in the top side of the shell, the second opening being in the bottom side and having a tube affixed thereto, the tube having an axis aligned with the central passage, a one-piece molding defining a primary seal and a secondary seal positioned in the housing encompassing the central passage, the primary seal positioned in the housing around the first opening, the secondary seal being attached to and depending from the primary seal and defined by a generally cylindrical air tight tube terminating in a lower peripheral rim, the tube portion of the secondary seal being in the general form of upper converging and lower diverging planar wall sections which meet along a diametric sealing line defined by touching interior surfaces of the planar wall sections the lower planar walls comprising return planar walls which protect the integrity of the seal line by resisting the tendency of instruments to disturb the seal line by inverting the upper planar walls when passing through the seal valve.

* * * * *